United States Patent
Ingebrigtsen et al.

(10) Patent No.: US 6,821,252 B2
(45) Date of Patent: Nov. 23, 2004

(54) HARMONIC TRANSDUCER ELEMENT STRUCTURES AND PROPERTIES

(75) Inventors: Kjell Arne Ingebrigtsen, Trondheim (NO); Arne Ronnekleiv, Trondheim (NO)

(73) Assignee: G.E. Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/063,154

(22) Filed: Mar. 26, 2002

(65) Prior Publication Data

US 2003/0187352 A1 Oct. 2, 2003

(51) Int. Cl.[7] .............................................. A61B 8/00
(52) U.S. Cl. ....................................................... 600/459
(58) Field of Search ................................. 600/437, 440, 600/441, 458–459, 447, 466, 463, 472; 310/334–336, 36, 328, 321, 322; 29/25.3

(56) References Cited

U.S. PATENT DOCUMENTS

| | | | | |
|---|---|---|---|---|
| 4,276,491 A | * | 6/1981 | Daniel | 310/317 |
| 5,410,205 A | * | 4/1995 | Gururaja | 310/328 |
| 5,415,175 A | * | 5/1995 | Hanafy et al. | 600/459 |
| 5,638,822 A | * | 6/1997 | Seyed-Bolorforosh et al. | 600/459 |
| 5,685,308 A | * | 11/1997 | Wright et al. | 600/443 |
| 5,724,976 A | * | 3/1998 | Mine et al. | 600/459 |
| 5,825,117 A | * | 10/1998 | Ossmann et al. | 310/317 |
| 5,957,851 A | * | 9/1999 | Hossack | 600/459 |
| 6,409,667 B1 | * | 6/2002 | Hossack | 600/443 |
| 6,465,937 B1 | * | 10/2002 | Chen et al. | 310/360 |
| 6,467,140 B2 | * | 10/2002 | Gururaja | 29/25.35 |

OTHER PUBLICATIONS

Nico de Jong, et. al, Harmonic Imaging for Ultrasound Contrast Agents, 2000 IEEE Ultrasonics Symposium, pp. 1869–1876.

* cited by examiner

Primary Examiner—Francis J. Jaworski
(74) Attorney, Agent, or Firm—McAndrews, Held & Malloy, Ltd.

(57) ABSTRACT

A transducer element for ultrasound reception comprises a first active transducer layer connected to a first receiver, and a second active transducer layer laminated to the first active transducer layer and connected to a second receiver. A transducer element for ultrasound transmission comprises a first active transducer layer connected to a first transmitter, and a second active transducer layer laminated to the first transducer layer and connected to a second transmitter. Further aspects of the present invention include a transducer element for ultrasound transmission and reception, a transducer array for ultrasound transmission and reception, and methods for transmitting and receiving ultrasound signals.

61 Claims, 8 Drawing Sheets

| Transducer | Parameter | 4*(1-3) 100 Ω |
|---|---|---|
| Backing: | Z (MRayl) | 2 |
| Metal towards backing: | Z (MRayl)<br>c (m/s)<br>l (μm) | 30<br>3750<br>15 |
| Elem. a: | $L_{sa}$ (μH)<br>$C_{ca}$ (pF)<br>$R_{lsa}$ (Ω)<br>$Z^D$ (MRayl)<br>c (m/s)<br>h ($10^9$ V/m)<br>$\epsilon_r^S$<br>l (μm)<br>Area (mm$^2$) | 6<br>100<br>100<br>14.06<br>3569<br>1.626<br>888<br>140<br>3.0<br>(2 stk.) |
| Metal between sub-elements: | Z (MRayl)<br>c (m/s)<br>l (μm) | 20<br>3750<br>15<br>(3 stk.) |
| Elem. b: | $L_{sb}$ (μH)<br>$C_{cb}$ (pF)<br>$R_{lsb}$ (Ω)<br>$Z^D$ (MRayl)<br>c (m/s)<br>h ($10^9$ V/m)<br>$\epsilon_r^S$<br>l (μm)<br>Area (mm$^2$) | 16<br>100<br>100<br>14.06<br>3569<br>1.626<br>888<br>116<br>3.0<br>(2 stk.) |
| Metal towards front: | Z (MRayl)<br>c (m/s)<br>l (μm) | 30<br>3750<br>15 |
| Transf. 1: | Z (MRayl)<br>l / λ v/2.5MHz | 8.04<br>0.25 |
| Transf. 2: | Z (MRayl)<br>l / λ v/2.5MHz | 2.63<br>0.25 |

Received first harmonic signal from the pressure in Fig. 5 when using the response B11 in reception.

HARMONIC TRANSDUCER ELEMENT STRUCTURES AND PROPERTIES

BACKGROUND OF INVENTION

Ultrasound probes for medical imaging support typically up to 90% relative bandwidth. In ultrasound imaging the bandwidth in absolute terms is directly proportional to the achievable range resolution, whereas the ultrasound center frequency is inversely related to the achievable imaging range. High relative bandwidth is therefore desirable to obtain high range resolution at good image range. To image the human hearts of adults, children, and small babies, for example, it is often necessary to have three different probes with typical center frequencies of 2.5 Mhz, 5 Mhz, and 9 Mhz. With wider band probes, the range needed for these applications may be covered with two probes and, in addition, have more flexibility to optimize the transmit signal and the receive filtering to the requirements encountered in each imaging situation.

A limitation in the use of Doppler for measuring blood velocity and/or motion of tissue is often detection sensitivity, whereas the spatial resolution required for good tissue imaging is of less importance. One may wish to have the Doppler centered at, for example, 2 Mhz, whereas the imaging could be at frequencies ranging up to 5 Mhz, which can only be accomplished with probe bandwidths exceeding today's standard, or with probes showing two passbands: one used for Doppler measurements, and the other for imaging.

Detection of second harmonic signals generated in tissue is used by most ultrasound scanners on the market today. The second harmonic ultrasound beam is more narrow with suppressed sidelobes compared to the fundamental frequency beam. By enhancing the second harmonic signal and suppressing the fundamental in the receiver, the image quality is significantly improved. For optimum performance, the ultrasound transducer should be able to cover the fundamental frequency and the second harmonic frequency, both with high bandwidths.

It has been proposed by researchers that detection of ultrasound contrast agents could be significantly enhanced by using the strong nonlinear generation of the reflected ultrasound from contrast agents. The differentiation of contrast agent from tissue would be significantly improved by detecting the $3^{rd}$ and $4^{th}$ harmonic of the fundamental ultrasound frequency.

The above ultrasound applications require transducer technology which are either extremely wideband, or which can manage different frequencies in the transmit and the receive mode.

Current probe technologies are limited to bandwidths ranging from about 70% to 90%. In harmonic imaging, for example, the center frequency of the transmit pulse is positioned on the low frequency side of the transducer pass band. The second harmonic will then be positioned on the upper side of the probe pass band. The result is that the transmit pulse and the received harmonic pulse are both distorted in the transducer. The distortion leads to extended pulse duration with loss of range resolution in the image. Moreover, the distortion also causes irrecoverable loss of imaging sensitivity. The manufacturing variability in probe center frequency and bandwidth leads to variations in image quality, and to variation in insertion loss of the second harmonic detection. There is today no probe technology commercially available for the detection of $3^{rd}$ and $4^{th}$ harmonic frequencies.

Another important issue in harmonic enhanced image quality is the need to suppress harmonic frequencies in the transmit signal. The image quality advantage is obtained almost solely from harmonics generated in tissue. Transmitted harmonic signals will have more or less the same sidelobes as the fundamental frequencies, and the advantage to the image quality of a narrow beam is lost. Thus there is a need for a transducer and transmitter that are designed together to obtain transmit pulses which are optimum for harmonic imaging.

The reflected signal from tissue contains frequencies from the fundamental and from the harmonics. Near the probe, the harmonic has not been able to develop, and most of the energy is on the fundamental frequency. Deeper into the body (typically beyond one centimeter or so) the harmonic signal has developed to provide a strong echo which can be extracted from the fundamental in the receiver to give the image quality improvements. At large depths, the second harmonic is more heavily attenuated than the fundamental, and most of the reflected energy is on the fundamental frequency. Since the ratio of harmonic to fundamental power increases with the output transmit power, the range where the harmonic is effective for imaging will also increase with the output transmit power. The mix of energy in different frequency bands thus varies with the fundamental frequency, the transmit pulse power, the attenuation in tissue, and the imaging depth range. Therefore, the signal received back is so greatly modified that a simple element design is typically not optimum both for transmission and reception at all depths.

One approach to harmonic imaging is described by de Jong et al. (2000 IEEE Ultrasonics Symposium 1869–1876). De Jong et al. made a dual-frequency array transducer. The transducer comprised two types of transducer elements, the two types of elements having different center frequencies. The transducer had 48 of each kind of element, the elements being interleaved with adjacent side-by-side elements having a different center frequency. The De Jong et al. configuration leads to a large transducer footprint, which is a disadvantage in most applications.

Another conventional device comprises a stack of two transducers on top of each other. The transducers are tightly coupled acoustically because they are laminated into a sandwich. Each transducer is connected to either an instrument transmitter or a receiver but not to both a transmitter and a receiver.

SUMMARY OF INVENTION

An embodiment of the present invention comprises a transducer element for ultrasound transmission and reception. A first active transducer layer is connected to a first receiver and a first transmitter. A second active transducer layer is laminated to the first active transducer layer and is connected to a second receiver and a second transmitter. The transducer element may comprise passive circuitry wherein a first pulse and a second pulse are processed by the passive circuitry so as to have one or more of the following properties prior to being combined into a single ultrasound pulse: different amplitudes, different time delays, and different shapes. Each active layer may be connected to a separate voltage source when the transducer element is in transmit mode. The transducer element may comprise a switch for switching the transducer element from transmit mode to receive mode. The tuning circuitries applied to the transducer layers in transmit may depend upon the mode of operations, and may for example be different for imaging, Doppler, and color flow. Likewise the tuning circuitries applied to the transducer layers during reception may be different from those applied in transmit, and the tuning circuitries may be different in different modes of operation. Switches may be used to facilitate connection to the appropriate tuning circuitries.

Another embodiment of the present invention comprises a plurality of transducer elements configured into an array to provide electronic beam steering and focusing. The various elements may be arbitrarily located with respect to each other. However, in the most common structures the transducer elements are organized in a row to facilitate beam steering and focusing in an arbitrary direction within a sector in a plane, or the transducer elements may be organized in a matrix to facilitate beam steering and focusing into a volume. The various elements may have different surface area, and/or different first and second active laminated transducer layer materials and/or different thicknesses. The first and second active laminated transducer layer of each element may be connected to separate independently programmable transmitters and receivers with separate switchable tuning circuitry. The various transmitters can be programmed to deliver signals with different amplitudes, different time delays, and different envelopes prior to becoming combined into a single acoustic transmit signal which is better optimized for imaging across the complete imaging scenario. The transducer array may comprise passive circuitry to reduce non-fundamental frequencies in the ultrasound pulse produced by combining the signals from the first and second transmitters. The transducer array may process signals from each active transducer layer separately to provide simultaneous display of a region with different receive beam forming and filtering. The transducer array may combine filtered and amplified receive signals from each active transducer layer before display to enhance image quality. The transducer array may combine filtered and amplified receive signals from each active transducer layer before display to display specific signal features. The transducer array may combine filtered and amplified receive signals from each active transducer layer before display to display harmonic frequency generation and imaging of contrast agents within tissue.

Still further aspects of the invention include a method of transmitting an ultrasound pulse comprising the step of providing a transducer element having a first active transducer layer connected to a first transmitter and a second active transducer layer laminated to the first active transducer layer and connected to a second transmitter. Other steps include transmitting a first signal into the first active transducer layer and transmitting a second signal into the second active transducer layer.

Another aspect of the present invention is a method of transmitting and receiving an ultrasound pulse. The method may include the step of providing a transducer array comprising a plurality of transducer elements wherein at least two transducer elements comprise a first active transducer layer connected to a first receiver and a second active transducer layer laminated to the first active transducer layer and connected to a second receiver. Additional steps may include transmitting a first signal into the first active transducer layer of at least two transducer elements, transmitting a second signal into the second active transducer layer of at least two transducer elements, wherein the first and second active layers of the transducer elements transmit an ultrasound pulse, filtering and amplifying a first signal in the first receiver of at least two transducer elements, filtering and combining the signals to form a first focused signal, filtering and amplifying a second signal in the second receiver of at least two transducer elements, filtering and combining the signals to form a second focused signal, and then optionally additional filtering of the two focused signals before the signals are combined into a final focused signal.

BRIEF DESCRIPTION OF DRAWINGS

The foregoing summary, as well as the following detailed description of the preferred embodiments of the present invention, will be better understood when read in conjunction with the appended drawings. For the purpose of illustrating the preferred embodiments of the present invention, there is shown in the drawings, embodiments which are presently preferred. It should be understood, however, that the present invention is not limited to the arrangements and instrumentality shown in the attached drawings.

DETAILED DESCRIPTION

Figure 1:
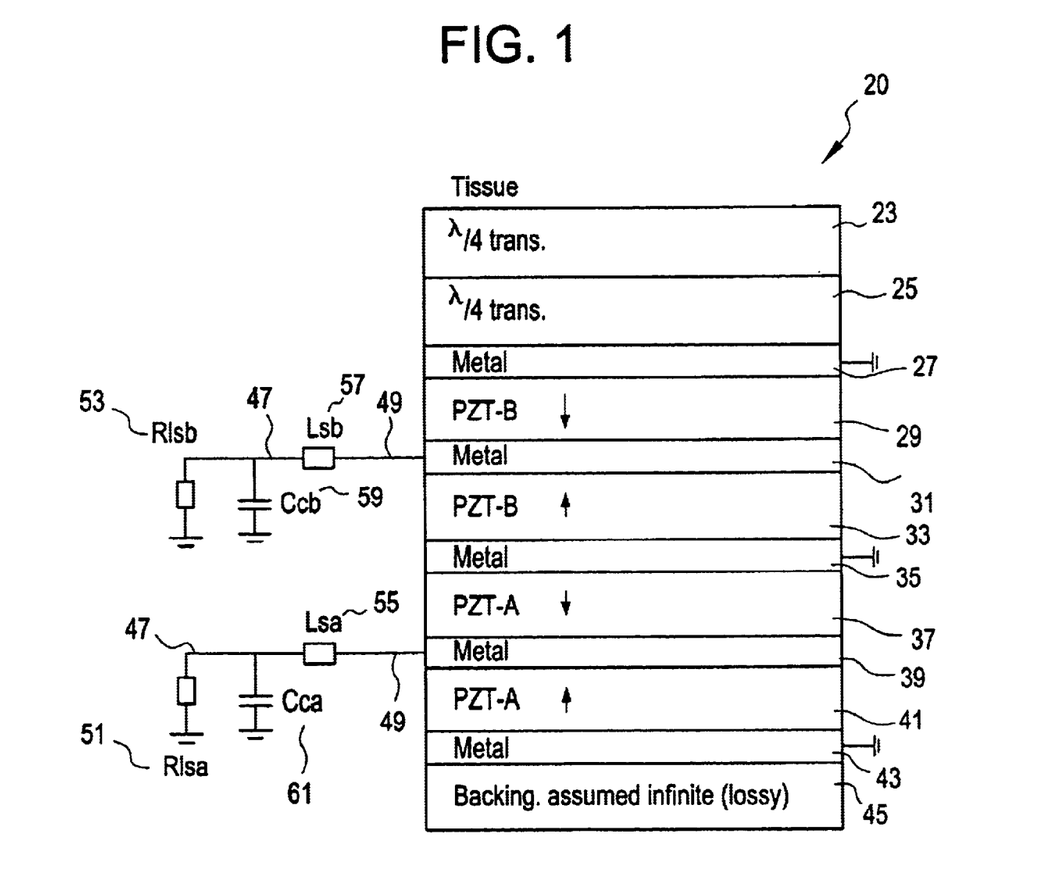
FIG. 1 depicts a sectional view of a transducer element formed in accordance with one embodiment of the present invention with tuning circuitry shown schematically.

An embodiment of the present invention is shown in FIG. 1 and may be used for optimizing second harmonic or "octave" imaging or for other uses.

FIG. 1 shows schematically a vertical cut through an element 20 of one of the embodiments of the present invention. The element 20 of FIG. 1 includes first and second transformer layers 23, 25. Alternatively, a single transformer layer may be used in the element 20. Following the transformer layers 23, 25 are a first metal layer 27, a first PZT-B composite layer 29, a second metal layer 31, and a second PZT-B layer 33. The poling directions of the first and second PZT-B composite layers 29, 33, active layers, are shown by arrows and may be different than shown in FIG. 1 but should be opposite one another. A third metal layer 35 is positioned between the second PZT-B layer 33 and a first PZT-A layer 37. A fourth metal layer 39 is positioned between the first PZT-A layer 37 and a second PZT-A layer 41. The poling directions of the first and second PZT-A composite layers, active layers 37, 41, are shown by arrows and may be different than shown in FIG. 1 but should be opposite one another. The designation of the PZT layers as A and B layers is to signify two different pairs of active layers, but does not mean particular differences. A fifth metal layer 43 is positioned between the second PZT-A layer 41 and a backing layer 45. The backing layer 45 is assumed to absorb all energy emitted into it.

The structure of tuning circuits 47 and electrical connections 49 to the transducer element 20 are also shown in FIG. 1. Suitable acousto-electric properties of the different layers in the structure are given in the table shown in FIG. 2. The resistances Rlsa 51 and Rlsb 53 are (a) the input impedances of amplifiers when the transducer element 20 is in receive mode or (b) the output impedances when the transducer element 20 is in transmit mode. Lsa 55 and Lsb 57 represent inductors in the probe. Ccb 59 and Cca 61 represent the capacitances of a cable connected to the probe.

Figure 2:
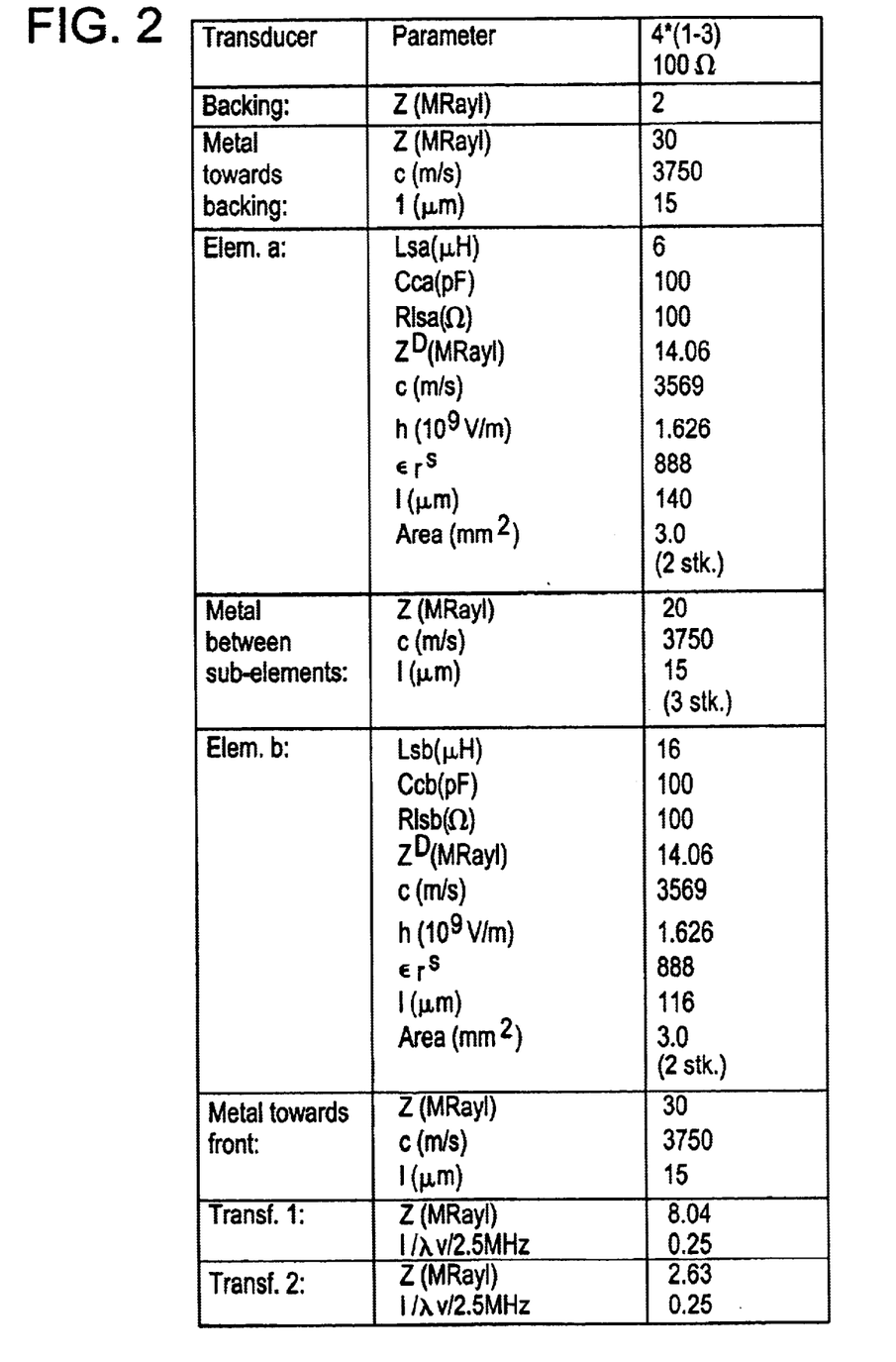
FIG. 2 is a table of properties of the parts comprising the transducer element of FIG. 1.

Acousto-electric properties in other transducer elements having a similar arrangement to the arrangement of FIG. 1 may differ significantly from the properties shown in the table in FIG. 2, which is only one example of properties.

In receive mode, signals from each layer A 37, 41 and each layer B 29, 33 in FIG. 1, are preferably focused in independent focusing electronics before the signals are filtered and combined. Having two layers for A (37, 41) and two layers for B (29, 33), rather than a single layer for each, lowers the electrical impedance of each active transducer layer because the two A layers 37, 41 are in parallel and the two B layers 29, 33 are in parallel. This configuration with the two A layers and the two B layers may simplify implementation of matching circuitry for some applications.

By focusing before the signals are combined, the focused signals may undergo one or more of the following before the focused signals are added: weighting, delaying, phase shifting and filtering. Structuring the processing in a way that at least some processing is performed prior to combining the signals will help attain optimum amplitude response and noise properties of the combined signal. In addition to shaping the output signal for desired properties, the filtering, which is optional, may also serve to remove noise contributions from frequency regions in the signal from one layer where the contribution to useful signals is small.

A structure similar to the embodiment of FIG. 1 may also be optimized for other purposes, such as reception on the third harmonic of the transmit frequency, or to deal with the mismatch between high element impedances and large cable capacitances often seen in 1.5D and 2D imaging systems.

Figure 3:
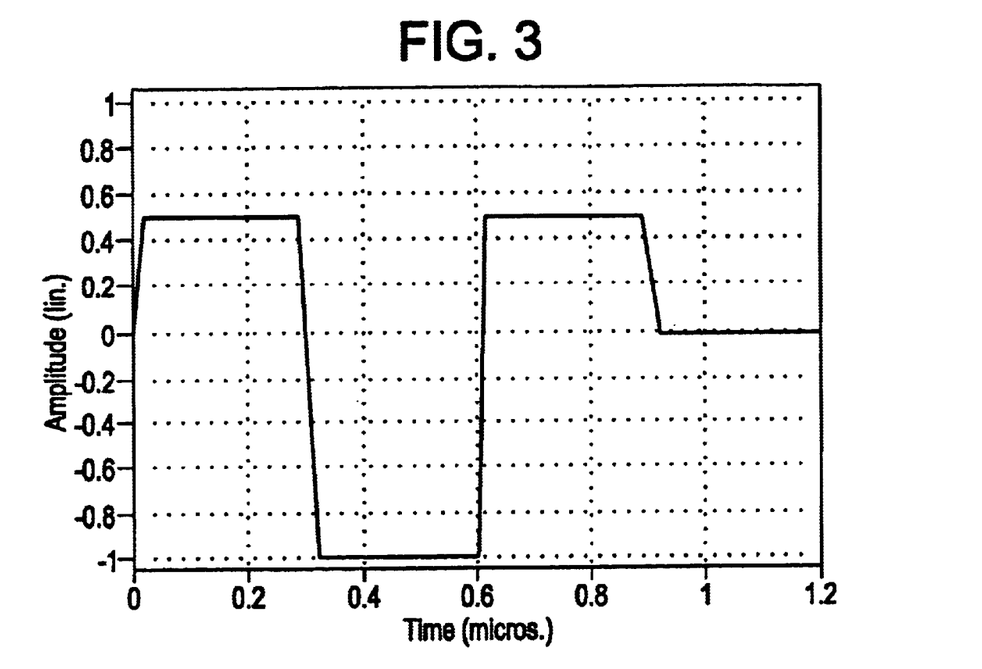
FIG. 3 is a graph of the shape of the exciting pulse for the transducer elements of FIG. 1.
Figure 4:
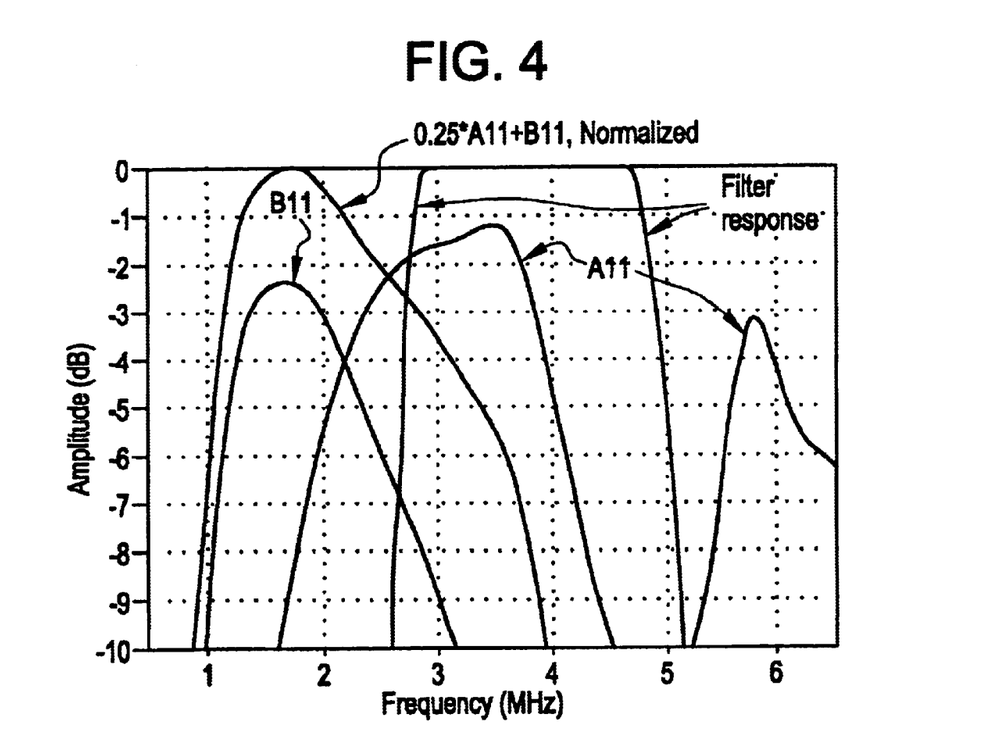
FIG. 4 is a graph of the frequency responses for the transducer element of FIG. 1 and a filter response.

The frequency response and other performance features of the embodiment of FIG. 1 are shown in FIGS. 3–8. FIG. 3 is a graph of the shape of the exciting pulse for the transducer element 20 of FIG. 1. FIG. 4 is a graph of the frequency responses for the transducer element 20 and a filter response. A11 and B11 are the responses for the double elements A 37, 41 and B 29, 33 with their nominal 100-Ohm load. The curve marked 0.25*A11+B11 shows the shape of the response $v_{tr}$ ($\omega$) as given in Eq.(1) below. The curve marked "Filter Response" shows the amplitude response of a linear phase filter used in the simulation of reception of a $2^{nd}$ harmonic response, see FIG. 8.

Figure 5:
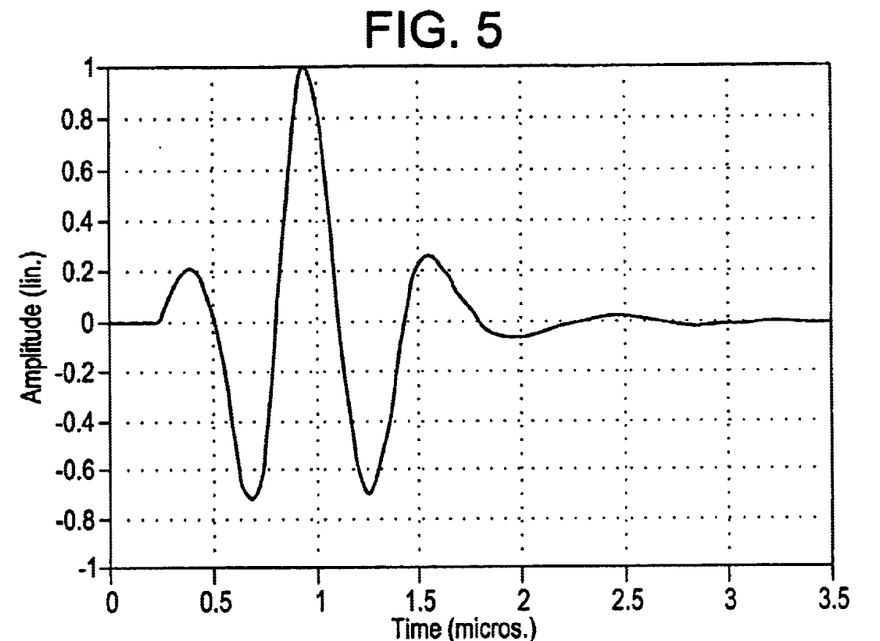
FIG. 5 is a graph of sound pressure in water/tissue when the response $v_{tr}$ and the pulse shape shown in FIG. 3 is used in transmission.
Figure 6:
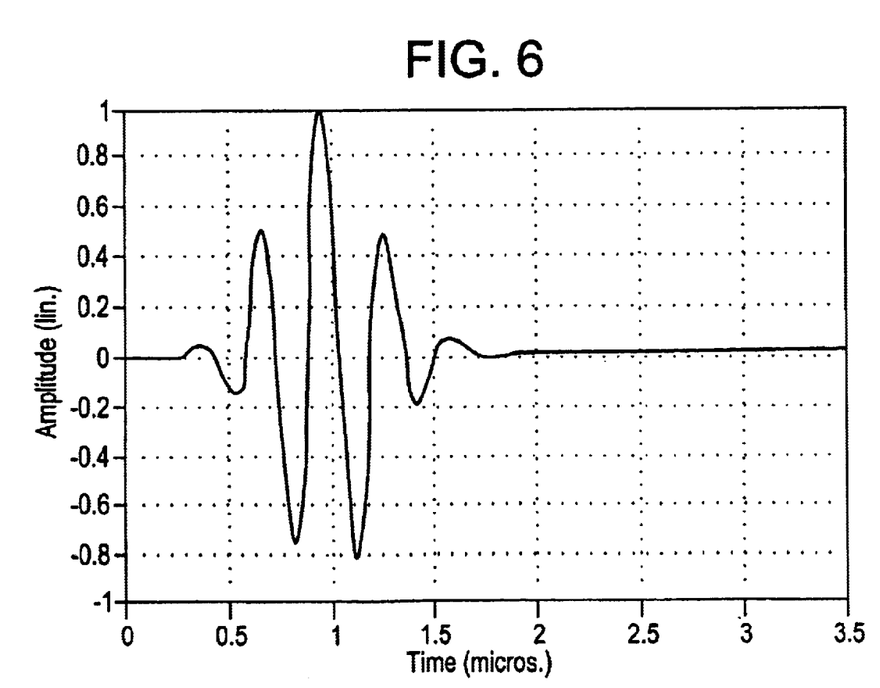
FIG. 6 is a graph of the shape of the $2^{nd}$ harmonic signal in tissue, as derived from the pressure shape shown in FIG. 5 using the procedure given by Eq. (2).
Figure 7:
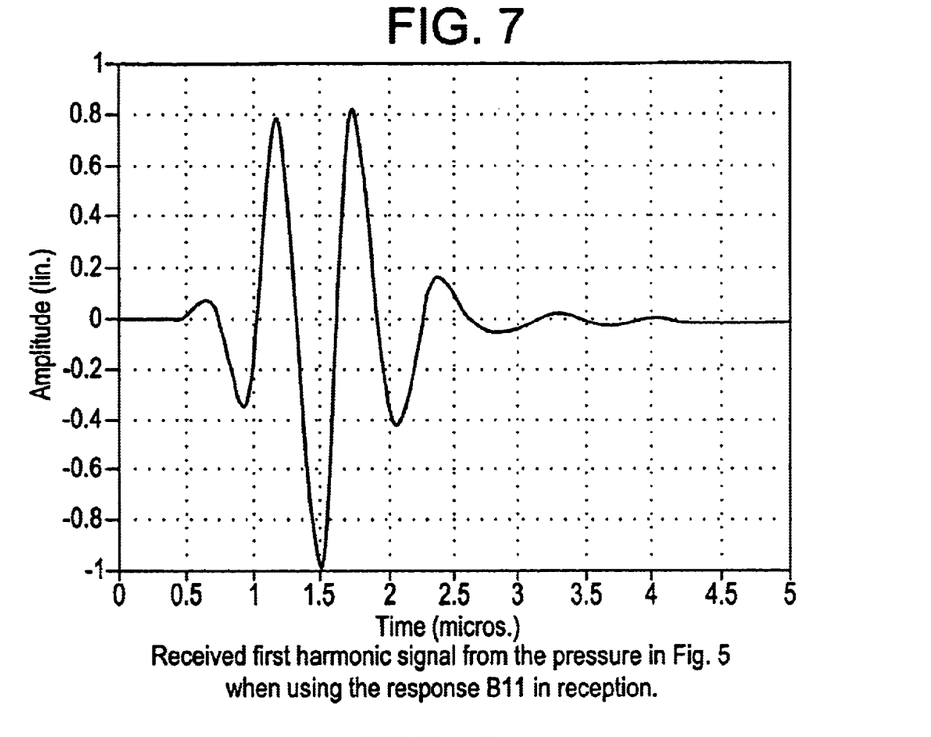
FIG. 7 is a graph of a received first harmonic signal from the pressure in FIG. 5, when using the response B11 in reception.

FIG. 5 is a graph of sound pressure in water/tissue when the response $v_{tr}$ ($\omega$) and the pulse shape shown in FIG. 3 is used in transmission. FIG. 6 is a graph of the shape of the $2^{nd}$ harmonic signal in tissue, as derived from the pressure shape shown in FIG. 5 using the procedure given by Eq. (2). FIG. 7 is a graph of a received first harmonic signal from the pressure in FIG. 5, when using the response B11 in reception.

Figure 8:
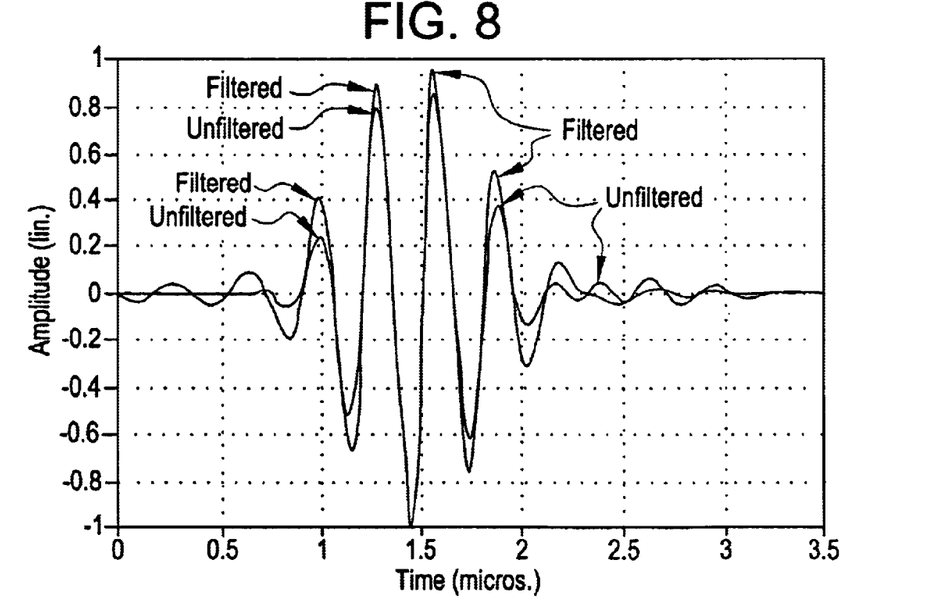
FIG. 8 is a graph of received $2^{nd}$ harmonic signals from the signal shown in FIG. 6 in two cases.

FIG. 8 is a graph of received $2^{nd}$ harmonic signals from the signal shown in FIG. 6 in two cases. In case 1, only the response A11 is used in reception and the received signal is marked "Unfiltered." In case 2, the response A11 combined with the filter response shown in FIG. 4 and marked "Filter response" is used in reception and the resulting received signal is marked "Filtered."

FIGS. 3–8 show the transmit pulse, the frequency response of the system, and different pulse shapes in the system when used in a way which gives an output signal which comprises only the second harmonic signal generated in tissue, FIG. 8, and the echoes without any second harmonic generation in FIG. 7. The effect on the received pulse shape of adding a filter (see FIG. 4) to further suppress the first harmonic signal component in the second harmonic output signal is also shown (FIG. 8). In this case, the transmit pulse is applied to both layers, but with different weights and no difference in time delay. The relative weight given to active layers A 37, 41 compared to active layers B 29, 33 is $A_{tr}$=0.25, which gives a frequency response in transmission $v_{tr}$ given by:

$$v_{tr}(\omega)=A_{tr}v_a(\omega)+v_b(\omega) \tag{1}$$

where $v_a$ ($\omega$) is the response of active layers A 37, 41 with active layers B 29, 33 connected to Rlsb (A11), and $v_b$ ($\omega$) is the response of active layers B 29, 33 with active layers A 37, 41 connected to Rlsa (B11). Note that the curve in FIG. 4 does not show the level of the insertion loss of this response, only its shape.

Depending on the range, different combinations of the received pulses shown in FIG. 7 and FIG. 8 may be used, to give the optimum picture quality. This requires range-dependent combination of the two responses.

In the calculations, the generation of the second harmonic signal is done as follows: a pressure p(t) which is zero for t<0 was assumed, and the Fourier transform was taken to obtain the spectrum P($\omega$). The pre-envelope, $p_{pr}$ (t,) of the signal was computed as the inverse Fourier transform of only the spectrum for positive $\omega$. The second harmonic of the pressure signal, $p_2$ (t), was then obtained as the real part of the pre-envelope squared (see equations below). The procedure as given here does not give the correct magnitude of the second harmonic signal.

$$P(\omega) = \int_0^\infty p(t)\exp(i\omega t)dt \tag{2}$$

$$p_{pr}(t) = \frac{1}{2\pi}\int_0^\infty P(\omega)\exp(-iwt)dw$$

$$p_2(t) = \text{Re}[(p_{pr}(t)^2)]$$

In embodiments of the present invention, the active transducer layers may each have different properties. For instance, active A layer 37 may have different properties from active A layer 41. Active B layer 29 may have different properties than active B layer 33. One or both of the active A layers 37, 41 may have different properties than one or both of the active B layers 29, 33. Varied properties may include, but are not limited to, one or more of the following: acoustic properties, thicknesses, PZT materials. Alternatively, A and B active layers 29, 33, 37, 41 may have identical properties. The B active layers 29, 33 are connected to a transmitter and a receiver, and the A active layers 37, 41 are connected to a transmitter and a receiver. The transmitter and receiver filters of the active A layers 37, 41 may be different from the transmitter and receiver filters of the active B layers 29, 33. By applying different transmit signals to the various active layers in the transducer stack, a resulting combined output ultrasound signal which is more optimum for many applications may be synthesized.

Some embodiments of the present invention achieve large bandwidths, as is desired in harmonic imaging. Some embodiments of the present invention comprise a transducer element that is divided into several layers which are connected to separate transmitters with separate tuning circuitry or receivers with separate tuning circuitry. An example with two layers is given below. It is directed toward harmonic imaging, transmitting on the first harmonic around 1.67 Mhz and receiving on the second harmonic.

If the acoustic output $O_i$ (f) from an electric signal $E_i$ (f) applied to transducer layer "i" through an electric tuning circuitry $D_i$ (f) is $$O_i(f)=D_i(f) \times T_i(f) \times E_i(f) \qquad (3)$$

where $T_i$ (f) is the transducer transmit transfer function, the overall response will be $$O(f)=\text{Sum over } i \text{ of } \{D_i(f) \times T_i(f) \times E_i(f)\} \qquad (4)$$

In some embodiments, it is possible to switch between different tuning circuits in transmission to obtain output signals with different characteristics. Likewise, the various layers in the stack may be connected to separate receivers with separate filter functions and gains before the receiver outputs are coherently combined to yield the desired output signal. If the input acoustic signal to the receive transducer is U(f), the transfer function of transducer layer "i" is $R_i$ (f), the filter and gain function applied to the layer signal is $G_i$ (f), the combined receiver output M(f) is:

$$M(f)=\text{Sum over } i \text{ of } \{G_i(f) \times R_i(f) \times U(f)\} \qquad (5)$$

In some embodiments, parallel output channels with different $G_i$'s may be used to obtain output signals with different characteristics.

In some embodiments of the present invention, the two-transducer layers are connected to separate transmitters and receivers. The two transmitters and the two receivers may be synchronized in such a way that the resulting combined ultrasound transmit pulse and the combined electric receive pulse are optimized for harmonic frequency imaging.

Assume that each one of the two transducer layers have transmit impulse responses of $T_1$ (f) and $T_2$ (f) respectively, and likewise receive impulse responses $R_1$ (f) and $R_2$ (f). To optimize the overall performance the output ultrasound pulse may be:

$$O(f)=T_1(f) \times D_1(f) \times E_1(f) + T_2(f) \times D_2(f) \times E_2(f) \qquad (6)$$

where $D_1(f)$ and $D_2$ (f) are electric tuning responses, and $E_1$ (f) and $E_2$ (f) are the input signals from each separate transmitter chosen to optimize O(f). Generally $E_1$ (f) and $E_2$ (f) are complex signals with different amplitudes and phases.

A receive signal M(f) which is a complex sum of the receive signals from the two transducers may be formed:

$$M(f)=[G_1(f) \times R_1(f) + G_2(f) \times R_2(f)] \times U(f) \qquad (7)$$

where $G_1$ (f) and $G_2$ (f) are complex weighting functions given to the signal from each transducer layer before the signals are summed together.

In a realistic imaging situation, $E_1$ (f) and $E_2$ (f) may be chosen to give an O(f) which is a short ultrasound pulse for excellent range resolution and free of harmonic frequency components. $G_1$ (f) and $G_2$ (f) will be chosen to optimize the harmonic signal. However under certain circumstances such as in the near field or in the far field it may be desirable to include a component of the reflected signal on the fundamental frequency. Then two separate receive functions $M_1$ and $M_2$ may be formed which represent respectively the fundamental and second harmonic component which may then be combined to the yield the final image.

The principle may be extended to more than two transducer layers. In the case of N layers the summation will be:

$$O(f)=\text{Sum over } n \; [T_n(f) \times D_n(f) \times E_n(f)]. \qquad (8)$$

and $$M(f)=\text{Sum over } n \; \{G_n(f) \times R_n(f)\} \times U(f). \qquad (9)$$

Figure 9:
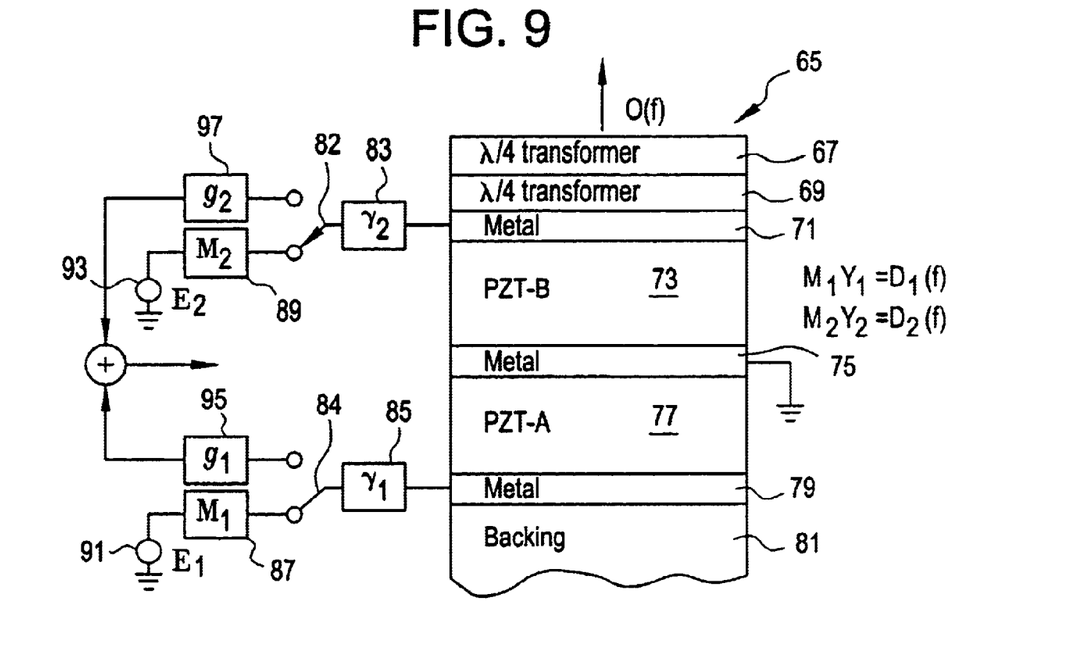
FIG. 9 depicts a sectional view of a transducer element formed in accordance with another embodiment of the present invention with tuning circuitry shown schematically in transmission mode.

FIG. 9 shows an alternative embodiment of the present invention. A transducer element 65 in FIG. 9 comprises the following layers: a first λ/4 transformer 67, a second λ/4 transformer 69, a first metal layer 71, a PZT-B layer 73, a second metal layer 75, a PZT-A layer 77, a third metal layer 79, and a backing 81. A single transformer layer may be used in place of the first and second transformer layers 67, 69. The poling direction of the two PZT layers 73, 77, the active layers, may be in either direction. The first metal layer 71 is connected to passive circuitry $\gamma_2$ 83 such as an inductor, capacitor and/or resistor. $\gamma_2$ 83 comprises matching circuitry. The third metal layer 79 is connected to passive circuitry $\gamma_1$ 85 which may be different than or the same as $\gamma_2$ 83. In transmission mode, as seen in FIG. 9, $\gamma_1$ 85 and $\gamma_2$ 83 are connected to respective matching circuitry $M_1$ 87 and $M_2$ 89. Voltage sources $E_1$ 91 and $E_2$ 93 provide alternating signals complex pulse forms to respective matching circuitry ($M_1$ 87 and $\gamma_1$ 85) or ($M_2$ 89 and $\gamma_2$ 83) resulting in transmission of an ultrasound pulse through the transducer element 65, as indicated by the O(f) arrow upward.

The metal layers 71, 75, 79 are primarily electrical contacts between the active layers 73, 77 and the matching circuitry. The metal layers 71, 75, 79 may also have some effect on the frequency response of the transducer element 65. The material parameters listed in the table of FIG. 2 for the embodiment of FIG. 1 are generally suitable for the embodiment of FIG. 9. One change, however, would be the thickness of the active layers 73, 77. For the embodiment of FIG. 1, each active PZT-A layer 37, 41 had a thickness (I) of about 140 μm whereas the thickness (I) of the active PZT-A layer 77 in the embodiment of FIG. 9 would be about twice as thick or about 280 μm. Parameters other than those shown in the table of FIG. 2 may also be suitable for the embodiment of FIG. 9.

The frequency transfer function in transmission for the embodiment of FIG. 9 may then be written $$M_{1\gamma 1}=D_1(f) \times T_1(f) \text{ and } M_{2\gamma 2}=D_2(f) \times T_2(f) \qquad (10)$$

where f is the frequency, $D_1$ and $D_2$ the electronic tuning circuitry responses, and $T_1$ and $T_2$ are the transmit transfer functions of the active transducer layers 1 and 2.

The matching circuitry elements $M_1$ 87, $\gamma_1$ 85, $g_1$ 95, $M_2$ 89, $\gamma_2$ 83, and $g_2$ 97 are frequency dependent. Because the matching circuitry for the first active transducer layer 73 is separate from the matching circuitry of the second active transducer layer 77, one or more of the following may be performed before the signals are added: separate focusing, weighting, delaying, phase shifting and filtering.

A switch 82 or 84 may be in the probe (not shown) or on the instrument side of the cable. If the switch 82 is on the instrument side, then $\gamma_2$ 83 and $\gamma_1$ 85 include the cable and the electronics in the probe on either side of the cable. If the switch 82 or 84 is in the front of the probe, the cable will be in $g_2$ 97 and also part of $M_2$ 89 (and $g_1$ 95 and $M_1$ 87).

Figure 11:
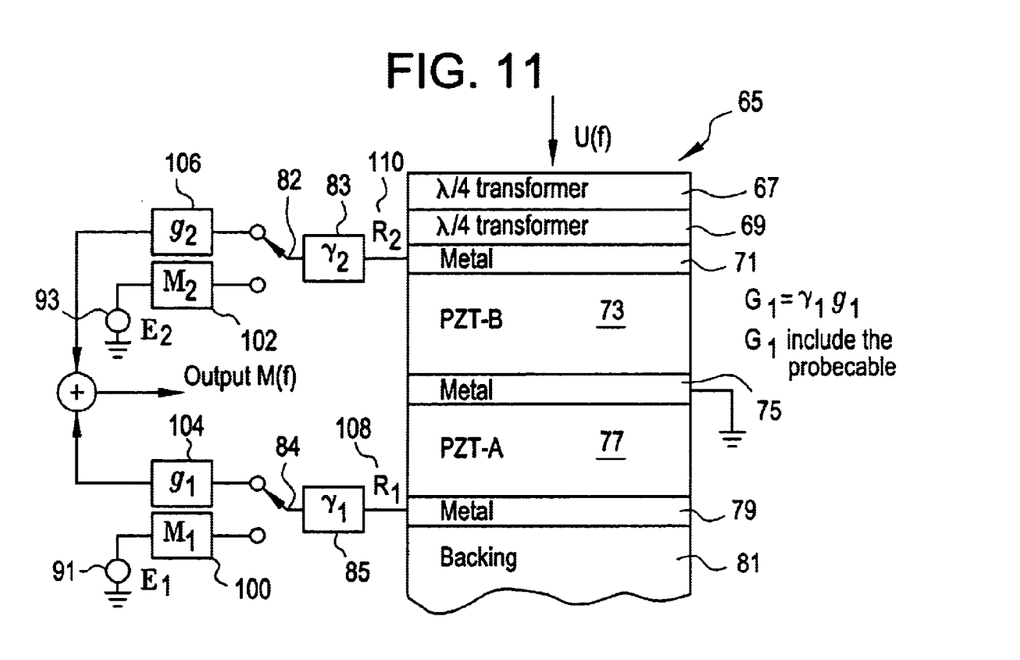
FIG. 11 depicts a sectional view of the transducer element and tuning circuitry of FIG. 9 shown in reception mode.

FIG. 11 illustrates the same transducer element 65 as shown in FIG. 9 but in reception mode rather than transmission mode. After an ultrasound pulse is sent, the switches 82 and 84 are moved so that echoes may be received. For ease of understanding, the matching circuitry of FIG. 11 is shown to have the same general matching circuitry elements as the matching circuitry of FIG. 9 (i.e., $M_1$, $M_2$, $g_1$, $g_2$, $\gamma_1$, $\gamma_2$). The response represented by the elements $\gamma_1$ and $\gamma_2$, however, are in general different in transmission (FIG. 9) from in reception (FIG. 11). The differences result, in part, from the change in load impedances between transmission and reception, $M_2$ vs. $g_2$, but it may be desirable for other reasons also to switch components in $\gamma_2$ when turning the transmission/reception switch. In reception mode, the matching circuitry is defined by:

$$G_i = \gamma_i g_i \text{ where } g_i \text{ or } \gamma_i \text{ includes the probe cable.} \quad (11)$$

G is the overall receive transfer function.

In reception mode, ultrasound echoes U(f) are received by the transducer element 65. The electrical signals $R_1$ 108 and $R_2$ 110 generated at the transducer contacts 79 and 71 depend on the transfer functions of the transducer as well as the electrical impedances represented respectively by the circuitries $\gamma_1$ 85, $g_1$ 104 and $\gamma_2$ 83, $g_2$ 106. $g_1$ 104 and $g_2$ 106 may include filtering and amplification, and may also include A/D conversion in which case the summation will be a digital summation, and the output M(f) a digital signal.

Figure 10:
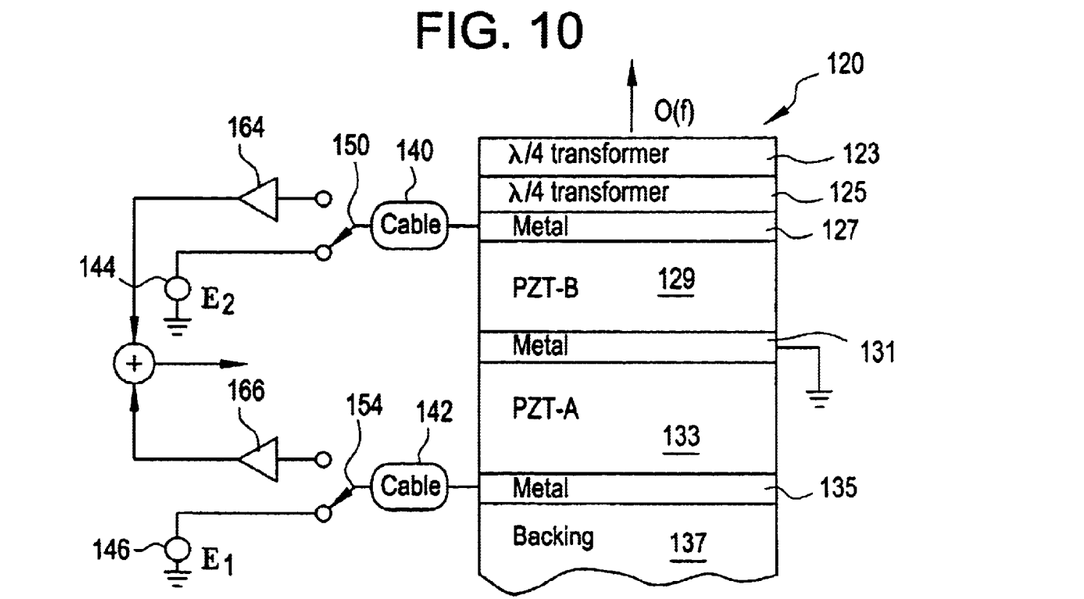
FIG. 10 depicts a sectional view of a transducer element formed in accordance with another embodiment of the present invention with tuning circuitry shown schematically in transmission mode.

FIG. 10 shows an alternative configuration of a transducer element. A transducer element 120 of FIG. 10 is in transmission mode and comprises a first $\lambda/4$ transformer layer 123, a second $\lambda/4$ transformer layer 125, a first metal layer 127, a PZT-B layer 129, a second metal layer 131, a PZT-A layer 133, a third metal layer 135, and backing 137. A single transformer layer may be used instead of two layers. The poling directions of the two PZT layers 129, 133, the active layers, may be in either direction. The first and third metal layers 127, 135 are connected to respective first and second cables 140, 142. In transmission mode, the first and second cables 140, 142 are switched to be connected to respective voltage source $E_2$ 144 and $E_1$ 146. Voltage sources $E_1$ 146 and $E_2$ 144 provide alternative signals or pulses. Voltage sources $E_1$ 146 and $E_2$ 144 provide power to respective third and first metal layers 135, 127 resulting in transmission of an ultrasound pulse through the transducer element 120, as indicated by the O(f) arrow upward. The ultrasound pulse is the sum of the pulses produced by the independent voltage sources $E_1$ 146 and $E_2$ 144. The material parameters listed in the table of FIG. 2 for the embodiment of FIG. 1 are generally suitable for the embodiment of FIG. 10. One change, however, would be the thickness (I) of the active layers 129, 133. For the embodiment of FIG. 1, each active PZT-A layer 37, 41 had a thickness (I) of about 140 μm, whereas the thickness of the active PZT-A layer 133 in the embodiment of FIG. 10 would be about twice as thick or about 280 μm. Parameters other than those shown in the table of FIG. 2 may be suitable for the embodiment of FIG. 10.

Figure 12:
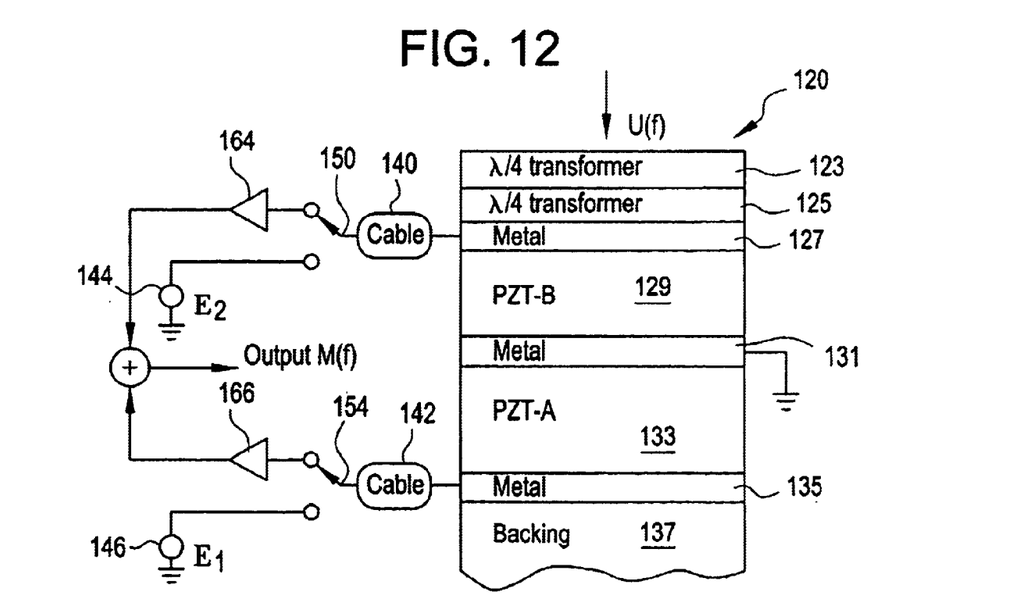
FIG. 12 depicts a sectional view of the transducer element and tuning circuitry of FIG. 10 shown in reception mode.

FIG. 12 is the same embodiment as shown in FIG. 10, however, FIG. 12 depicts reception mode. Soon after an ultrasound pulse is sent, switches 150 and 154 are moved so that echoes may be received. In reception mode, the first and second cables 140, 142 are connected to first and second amplifiers 164, 166. The amplifiers may be op amps. In reception mode, the transducer element 120 receives an ultrasound pulse U(f) that is transmitted through the first and third metal layers 127, 135, through respective first and second cables 140, 142 and through respective first and second amplifiers 164, 166. The signals exiting the first and second amplifiers 164, 166 are summed to produce and output. Following focusing and, in embodiments having digital encoding, following digital encoding, the signals are summed to produce output M(f). The summing step may be voltage summing or digital, depending on the type of signals.

For ease of understanding, the matching circuitry of FIG. 11 is shown to have the same general matching circuitry elements as the matching circuitry of FIG. 9 (i.e., elements are $M_1$, $M_2$, $g_1$, $g_2$, $\gamma_1$, $\gamma_2$). The response represented by the elements $\gamma_1$ and $\gamma_2$, however, are in general different in transmission (FIG. 9) from in reception (FIG. 11). The differences result, in part, from the change in load impedances between transmission and reception, $M_2$ vs. $g_2$, but it may be desirable for other reasons also to switch components in $\gamma_2$ when turning the transmission/reception switch. In reception mode, the matching circuitry is defined by:

$$G_i = \gamma_i g_i \text{ where } g_i \text{ or } \gamma_i \text{ includes the probe cable.} \quad (12)$$

G is the overall receive transfer function.

Regarding the embodiments of FIGS. 11 and 12, the first and second receivers may be associated with a filtering device. Analog-to-digital conversion may be performed before, after, or before and after a signal passes through the filtering device. The first and second receivers 164, 166 may each comprise an electrical filtering device to optimize a combined received pulse prior to image coding.

Regarding the embodiment of FIG. 9, a pulse from the first active transducer layer 73, and a pulse from the second active transducer layer 77 may be combined into a single ultrasound pulse. Regarding the embodiment of FIG. 10, a pulse from the first active transducer layer 129, and a pulse from the second active transducer layer 133 may be combined into a single ultrasound pulse. The transducer elements 65, 120 may comprise passive circuitry wherein a first pulse and a second pulse are processed by the passive circuitry so that prior to being combined into a single pulse at least one of the following is given to the pulses: different amplitudes, different time delays, and different shapes. The first and second transmitters 144, 146 may optimize a combined ultrasound transmit pulse for harmonic frequency imaging by reducing frequency components beyond a fundamental frequency band in a transmitted pulse, or the first and second transmitters 144, 146 may optimize the combined output pulse for other applications.

Although the embodiments of FIGS. 9–12 had only two active layers, more active layers may be included in a transducer element. Only two active layers were shown in order to avoid obscuring the fundamental features of the embodiments of FIGS. 9–12. In a transducer element comprising more than two active layers, two or more of the active layers may each have matching circuitry connected thereto, allowing the achievement of the advantages discussed above in connection with the embodiments of FIGS. 9–12.

Figure 13:
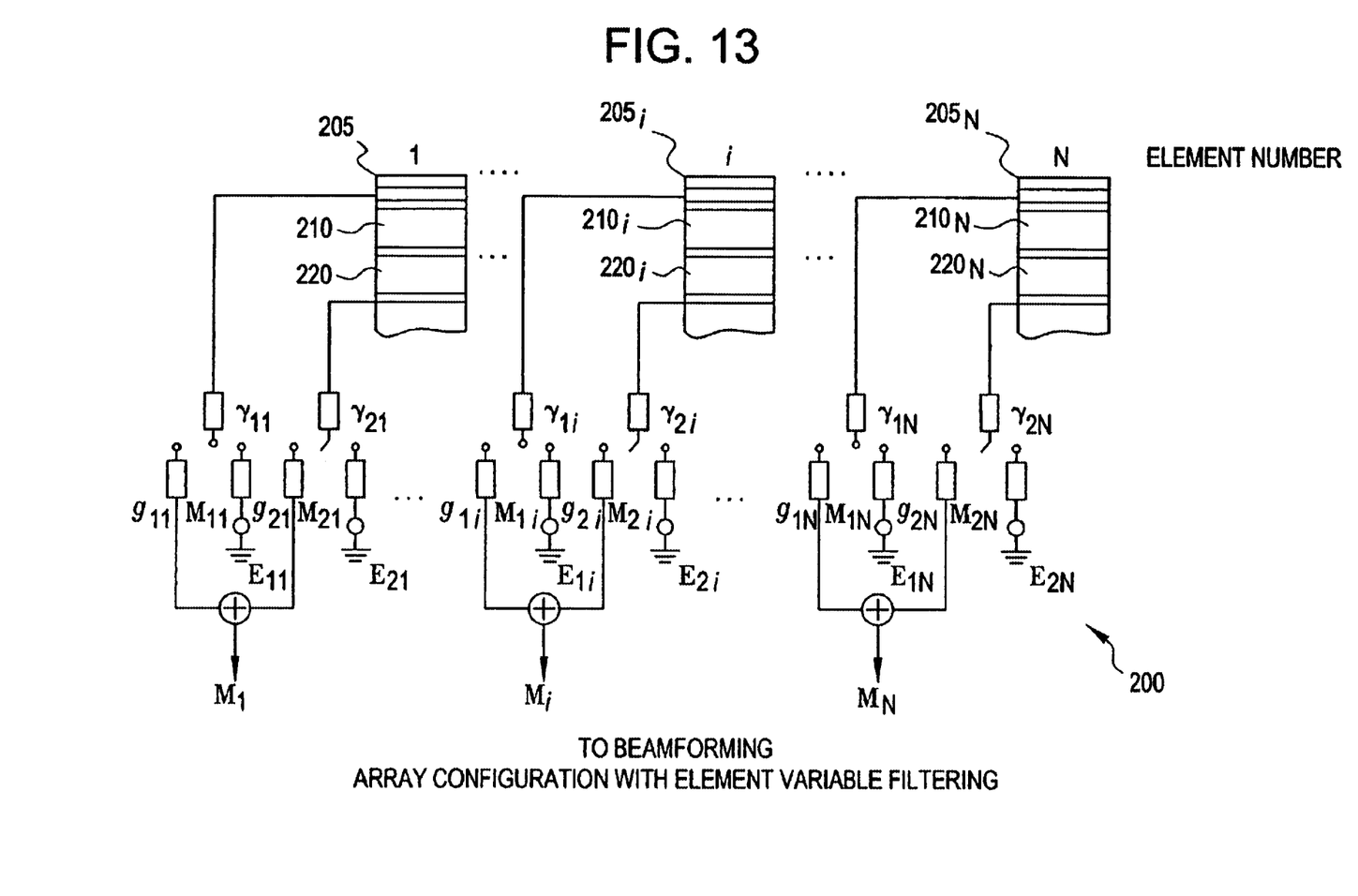
FIG. 13 depicts a schematic of a transducer array formed in accordance with an embodiment of the present invention.

FIG. 13 shows an array configuration 200 of one embodiment of the present invention comprising N transducer elements 205. The N transducer elements 205 may each be connected to circuitry such as the matching circuitry shown attached to the transducer elements of FIGS. 1 and 9–12. The transducer elements depicted in FIG. 13 are connected to circuitry most similar to the circuitry of FIGS. 9 and 11, but other matching circuitry may be suitable. Although the transducer elements 205 of FIG. 13 are not shown in great detail, the transducer elements 205 have a first active layer 210 and a second active layer 220, both of which are connected to separate tuning circuitry.

The transducer array 200 may comprise a first transducer element 205 having a first active layer 210 that comprises different material than a first active layer 210 of a second transducer element 205. The transducer array 200 may comprise a first transducer element 205 having a second active layer 220 that comprises different material than a second active layer 220 of a second transducer element 205. The transducer array 200 may comprise a first transducer element 205 having a first active layer 210 that comprises different material than a second active layer 220 of the first transducer element 205.

A first receiver and a second receiver may have different electrical properties from each other in an array 200. The transducer array 200 may comprise a first active transducer layer 210 and a second active transducer layer 220 connected to circuitry having different electrical properties. The transducer array 200 may comprise a first active transducer layer 210 of a first element 205 connected to a circuit having different properties than a circuit connected to a first active transducer layer 210 of a second element 205. At least two of the elements 205 of the transducer array 200 may be connected to separate focusing electronics to provide independent focusing for each layer. The elements within one active layer may be connected to separate focusing electronics than the next active layer to provide independent focusing for each active layer. (Independent focusing in each active layer is not shown in the figure.) Independent focusing in each active layer enables efficient processing, such as delay, filtering, scaling, and/or phase shifting, which are common to signals from elements of the same active layer.

First and second receivers may each comprise electrical filtering capability to optimize a combined received pulse prior to image coding. The first and second transmitters and passive circuitry may be designed to modify respective first and second signals to reduce the non-fundamental frequencies in the combined ultrasound transmit pulse used for harmonic frequency imaging.

First and second active transducer layers 210, 220 in elements 205 may have the same frequency response as corresponding active transducer layers 210, 220 in symmetrically positioned transducer elements 205 of the array 200. Such an arrangement may obtain frequency variable apodization across the array 200 during transmission. For example, a linear transducer array may comprise N transducer elements 205 with elements positioned at positions 1–N. Assume that the active transducer layers of the transducer element 205 at position 1 have the same frequency response as the corresponding active transducer layers in the transducer element at position N. Assume further that the frequency response of the active layers of the transducer element 205 in position 2 and the frequency response of the active layers of the transducer element positioned at N–1 are the same. If that pattern of equal frequency responses is true for all transducer elements 205 positioned at 1 through N, then frequency variable symmetric apodization across the array 200 during transmission is obtained.

Transducer elements 205 of the transducer array 200 may comprise circuitry so that the transducer array 200 provides at least one of the following: receive amplification, receive filtering, receive focusing to signals from the different active transducer layers. The delay for focusing may be done digitally or by other methods. The transducer array 200 may display signals from each layer separately to provide simultaneous display of the same region with different receive beam forming and filtering.

The transducer array 200 may combine amplified and filtered receive signals before display to enhance image quality. The transducer array 200 may combine amplified and filtered receive signals before display to enhance other specific signal features. Thus the transducer array may for instance combine amplified and filtered receive signals before display to display harmonic frequency generation and imaging of contrast agents within tissue.

The transducer array 200 may, both in transmission and in reception, comprise passive circuitry to process a first pulse and a second pulse to have at least one of the following prior to being combined into a single pulse: different amplitudes, different time delays, and different shapes.

The transducer array 200 may be a linear array. Alternatively, the transducer array 200 may be a two-dimensional array.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A transducer element for ultrasound transmission and reception comprising:

a first active transducer layer connected to a first receiver and a first transmitter; and a second active transducer layer laminated to the first active transducer layer and connected to a second receiver and a second transmitter, wherein the first active transducer layer includes a first pair of composite layers and the second active transducer layer includes a second pair of composite layers.

2. The transducer element of claim 1, and comprising passive circuitry for processing a first pulse and a second pulse.

3. The transducer element of claim 2, wherein the passive circuitry provides the first pulse with a different amplitude than an amplitude of the second pulse prior to being combined into a single pulse.

4. The transducer element of claim 2, wherein the passive circuitry provides the first and second pulses with different time delays prior to being combined into a single pulse.

5. The transducer element of claim 2, wherein the passive circuitry provides the first pulse with a different shape than a shape of the second pulse prior to being combined into a single pulse.

6. The transducer element of claim 1, wherein each active layer is connected to a separate voltage source when the transducer element is in a transmit mode.

7. A transducer element for ultrasound transmission and reception comprising:

a first active transducer layer connected to a first receiver and a first transmitter;

a second active transducer layer laminated to the first active transducer layer and connected to a second receiver and a second transmitter, wherein the first active transducer layer includes a first pair of composite layers and the second active transducer layer includes a second pair of composite layers; and passive circuitry for processing a first pulse and a second pulse, wherein the passive circuitry in a transmit mode performs in accordance with the following equation: $M_{1\gamma 1}=D_1(f)T_1(f)$, wherein $M_1$ defines frequency dependent matching circuitry elements, $\gamma_1$ defines said passive circuitry including at least one of an inductor, a capacitor and a resistor, $D_1(f)$ defines electronic tuning circuitry responses, $T_1(f)$ defines a transmit transfer function and f defines a frequency.

8. A transducer element for ultrasound transmission and reception comprising:

a first active transducer layer connected to a first receiver and a first transmitter;

a second active transducer layer laminated to the first active transducer layer and connected to a second receiver and a second transmitter, wherein the first active transducer layer includes a first pair of composite layers and the second active transducer layer includes a second pair of composite layers; and passive circuitry for processing a first pulse and a second pulse, wherein the passive circuitry in a receive mode performs in accordance with the following equation: $G_1=\gamma_1 g_1$, wherein $G_1$ defines an overall receive transfer function and $\gamma_1$ or $g_1$ include said passive circuitry, wherein said passive circuitry includes at least one of an inductor, a capacitor, a resistor and a probe cable.

9. The transducer element of claim 1, and comprising a switch for switching the transducer element from a transmit mode to a receive mode.

10. The transducer element of claim 1, wherein the first and second receivers each are associated with at least one filtering device.

11. The transducer element of claim 10, wherein analog-to-digital conversion is performed at least one of before and after a signal has passed through the at least one filtering device.

12. The transducer element of claim 10, wherein filtering is performed prior to amplification of a signal by one of the receivers.

13. The transducer element of claim 10, wherein filtering is performed after amplification of a signal by one of the receivers.

14. The transducer element of claim 13, wherein filtering is performed before and after amplification of a signal by one of the receivers.

15. The transducer element of claim 1, wherein the first receiver comprises a first electrical filtering device and the second receiver comprises a second electrical filtering device, wherein the first and second electrical filtering devices optimize a combined received pulse prior to image coding.

16. A transducer element for ultrasound transmission and reception comprising;

a first active transducer layer connected to a first receiver and a first transmitter;

a second active transducer layer laminated to the first active transducer layer and connected to a second receiver and a second transmitter; and passive circuitry wherein a first pulse produced by the first transmitter and a second pulse produced by the second transmitter are processed by the passive circuitry prior to being combined into a single ultrasound pulse.

17. A transducer element for ultrasound transmission and reception comprising:

a first active transducer layer connected to a first receiver and a first transmitter;

a second active transducer layer laminated to the first active transducer layer and connected to a second receiver and a second transmitter; and wherein the first and second receivers each comprise an electrical filtering device to optimize a combined received electrical pulse prior to image coding.

18. A transducer array comprising:

a plurality of transducer elements wherein at least two transducer elements each comprise:

a first active transducer layer connected to a first receiver; and a second active transducer layer laminated to the first active transducer layer and connected to a second receiver, wherein a first active transducer layer of a first transducer element is connected to a circuit having different properties than a circuit connected to a first active transducer layer of a second transducer element.

19. The transducer array of claim 18, wherein the first active transducer layer of the first transducer element comprises different material than the first active transducer layer of the second transducer element.

20. The transducer array of claim 19, wherein a second active transducer layer of the first transducer element comprises different material than a second active transducer layer of the second transducer element.

21. The transducer array of claim 18, wherein electrical properties of the first receiver are different from electrical properties of the second receiver.

22. The transducer array of claim 18, wherein the first active transducer layer is connected to circuitry having different electrical properties than electrical properties of the second active transducer layer.

23. The transducer array of claim 18, wherein a second active transducer layer of the first element is connected to a circuit having different properties than the circuit connected to the first active transducer layer of the first element.

24. The transducer array of claim 18, in which the first active transducer layer of at least two of the elements are connected to focusing electronics that are separate and different from focusing electronics connected to the second active transducer layer of the same at least two elements to provide independent focusing.

25. The transducer array of claim 18, in which all of the active layers within a single element are connected to separate focusing electronics to provide independent focusing.

26. The transducer array of claim 18, wherein the first and second receivers of each element each comprise electrical filtering capability to optimize a combined received pulse prior to image coding.

27. The transducer array of claim 18, and comprising first and second transmitters.

28. The transducer array of claim 27, and comprising passive circuitry wherein a first pulse and a second pulse are processed by the passive circuitry to have at least one of the following: different amplitudes, different time delays, and different shapes, prior to being combined into a single ultrasound pulse.

29. The transducer array of claim 27, and comprising passive circuitry to reduce non-fundamental frequencies in the ultrasound pulse produced by combining the signals from the first and second transmitters.

30. The transducer array of claim 18, wherein the transducer array processes signals from each active transducer layer separately to provide simultaneous display of a region with different receive beam forming and filtering.

31. The transducer array of claim 18, wherein the transducer array combines filtered and amplified receive signals from each active transducer layer before display to enhance image quality.

32. The transducer array of claim 18, wherein the transducer array combines filtered and amplified receive signals from each active transducer layer before display to display specific signal features.

33. The transducer array of claim 18, wherein the transducer array combines filtered and amplified receive signals from each active transducer layer before display to display harmonic frequency generation and imaging of contrast agents within tissue.

34. The transducer array of claim 18, and comprising circuitry wherein a first pulse and a second pulse are processed by the circuitry to have at least one of the following: different amplitudes, different time delays, and different shapes, after being received by the first and second receivers.

35. The transducer array of claim 18, and comprising circuitry wherein a first pulse and a second pulse are processed by the circuitry to have at least one of the following: different amplitudes, different time delays, and different shapes, prior to being amplified in the first and second receivers.

36. The transducer array of claim 18, and comprising circuitry wherein a first pulse and a second pulse are processed by the circuitry to have at least one of the following: different amplitudes, different time delays, and different shapes, prior to and after being amplified in the first and second receivers.

37. The transducer array of claim 18, and comprising circuitry wherein a first pulse and a second pulse are processed by the circuitry to have at least one of the following: different amplitudes, different time delays, and different shapes, after being amplified in the first and second receivers.

38. The transducer array of claim 18, wherein the array is a linear array.

39. The transducer array of claim 18, wherein the array is a two-dimensional array.

40. A linear transducer array comprising N transducer elements wherein active transducer layers are arranged to obtain frequency variable apodization across the array during transmission,
wherein first and second transducer elements of the N transducer elements each include first and second active layers,
wherein a frequency response of first and second active layers of the first transducer element is equivalent to a frequency response of first and second active layers of the second transducer element,
wherein the second transducer element is symmetrically positioned relative to the first transducer element.

41. The transducer array of claim 40, and comprising passive circuitry wherein the passive circuitry provides at least one of the following: receive amplification, receive filtering, or receive focusing to signals from the different layers.

42. A method of transmitting an ultrasound pulse comprising the steps of:
providing a transducer element having a first active transducer layer connected to a first transmitter and a second active transducer layer laminated to the first active transducer layer and connected to a second transmitter,
wherein said first active transducer layer includes a first pair of composite layers and said second active transducer layer includes a second pair of composite layers;
transmitting a first signal into the first active transducer layer to produce a first ultrasound pulse; and
transmitting a second signal into the second active transducer layer to produce a second ultrasound pulse.

43. A method of receiving an ultrasound pulse comprising the steps of:
providing a transducer element comprising a first active transducer layer connected to a first receiver and a second active transducer layer connected to a second receiver;
receiving a first signal in the first receiver;
receiving a second signal in the second receiver; and
combining the first and second signals prior to image coding.

44. The method of claim 43, wherein at least one filtering step is performed prior to amplification in both of the receiving steps.

45. The method of claim 43, wherein at least one filtering step is performed after amplification in both of the receiving steps.

46. The method of claim 43, wherein at least one filtering step is performed prior to amplification in both of the receiving steps and at least one filtering step is performed after amplification in both of the receiving steps.

47. The method of claim 43, wherein at least one filtering step is performed after analog-to-digital conversion in both of the receiving steps.

48. The method of claim 43, wherein at least one filtering step is performed after amplification and before analog-to-digital conversion in both of the receiving steps.

49. The method of claim 43, wherein at least one filtering step is performed before analog-to-digital conversion in both of the receiving steps.

50. A method of transmitting and receiving an ultrasound pulse comprising the steps of:
providing a transducer element for ultrasound transmission and reception comprising:
a first active transducer layer connected to a first receiver and a first transmitter; and
a second active transducer layer laminated to the first active transducer layer and connected to a second receiver and a second transmitters,
wherein said first active transducer layer includes a first pair of composite layers and said second active transducer layer includes a second pair of composite layers;
transmitting a first signal into the first active transducer layer to produce an ultrasound pulse;
transmitting a second signal into the second active transducer layer to produce an ultrasound pulse; and
receiving a signal in at least one of the first and second receivers.

51. The method of claim 50, and comprising the step of filtering the signal after the signal is received in the at least one of the first and second receivers.

52. The method of claim 50, wherein:

the step of receiving a signal in at least one of the first and second receivers comprises the steps of receiving a first signal in a first receiver and receiving a second signal in a second receiver; and the step of combining the first and second signals follows a step of filtering the first and second signals prior to image coding.

53. A method of transmitting and receiving an ultrasound pulse comprising the steps of:

providing a transducer al-ray comprising:
a plurality of transducer elements wherein a first transducer element and a second transducer element each comprise a first active transducer layer connected to a first receiver and a second active transducer layer laminated to the first active transducer layer and connected to a second receiver;

transmitting a first signal into the first active transducer layer of the first transducer element to produce a first ultrasound pulse;

transmitting a second signal into the second active transducer layer of the first transducer element to produce a second ultrasound pulse;

transmitting a third signal into the first active transducer layer of the second transducer element to produce a third ultrasound pulse;

transmitting a fourth signal into the second active transducer layer of the second transducer element to produce a fourth ultrasound pulse;

receiving a first receive signal in the first receiver of the first transducer element;

filtering the first receive signal in the first transducer element;

receiving a second receive signal in the second receiver of the second transducer element;

filtering the second receive signal in the second transducer element;

combining the first receive signal with another receive signal of the first transducer element following the filtering of the first receive signal prior to image coding; and combining the second receive signal with another receive signal of the second transducer element following the filtering of the second receive signal prior to image coding.

54. The method of claim 53, wherein a first active transducer layer of a first transducer element comprises different material than a first active transducer layer of a second transducer element.

55. The method of claim 54, wherein a second active transducer layer of a first transducer element comprises different material than a second active transducer layer of a second transducer element.

56. The method of claim 54, wherein the first receiver and the second receiver have different electrical properties.

57. The method of claim 53, wherein the first active transducer layer and the second active transducer layer are connected to circuitry having different electrical properties.

58. The method of claim 53, wherein the first active transducer layer of a first element is connected to a circuit having different properties than a circuit connected to a first active transducer layer of a second element.

59. The method of claim 53, in which at least two of the active transducer layers are connected to separate focusing electronics to provide independent focusing.

60. The method of claim 53, in which all of the active layers within a single transducer element are connected to separate focusing electronics to provide independent focusing.

61. The method of claim 53, wherein the first and second receivers each comprise electrical filtering capability to optimize a combined received pulse prior to image coding.

* * * * *

UNITED STATES PATENT AND TRADEMARK OFFICE
CERTIFICATE OF CORRECTION

PATENT NO. : 6,821,252 B2
DATED : November 23, 2004
INVENTOR(S) : Ingebrigtsen et al.

It is certified that error appears in the above-identified patent and that said Letters Patent is hereby corrected as shown below:

Column 8,
Line 59, delete the symbol "$_y$" after "M1" and substitute therefore -- y --.
Line 59, delete the symbol "$_y$" after "M2" and substitute therefore -- y --.

Column 13,
Line 8, delete the symbol "$_y$" after "M1" and substitute therefore -- y --.

Column 16,
Line 54, delete "transmitters" and substitute therefore -- transmitter --.

Column 17,
Line 11, delete "al-ray" and substitute therefore -- array --.

Signed and Sealed this

Fifth Day of April, 2005

JON W. DUDAS
*Director of the United States Patent and Trademark Office*